(12) United States Patent
Palmer et al.

(10) Patent No.: US 10,835,274 B2
(45) Date of Patent: *Nov. 17, 2020

(54) MEDICAL ULTRASONIC CAUTERIZATION AND CUTTING DEVICE AND METHOD

(71) Applicant: Covidien LP, Mansfield, MA (US)

(72) Inventors: Matthew A. Palmer, Miami, FL (US); Derek Dee Deville, Coral Gables, FL (US); Kevin W. Smith, Coral Gables, FL (US)

(73) Assignee: Covidien LP, Mansfield, MA (US)

(*) Notice: Subject to any disclaimer, the term of this patent is extended or adjusted under 35 U.S.C. 154(b) by 157 days.

This patent is subject to a terminal disclaimer.

(21) Appl. No.: 15/958,624

(22) Filed: Apr. 20, 2018

(65) Prior Publication Data

US 2018/0256193 A1 Sep. 13, 2018

Related U.S. Application Data

(63) Continuation of application No. 14/971,329, filed on Dec. 16, 2015, now Pat. No. 9,980,742, which is a continuation of application No. 12/534,030, filed on Jul. 31, 2009, now Pat. No. 9,247,953.

(60) Provisional application No. 61/085,688, filed on Aug. 1, 2008.

(51) Int. Cl.
*A61B 17/285* (2006.01)
*A61B 17/32* (2006.01)

(52) U.S. Cl.
CPC .... *A61B 17/285* (2013.01); *A61B 17/320092* (2013.01); *A61B 2017/320093* (2017.08); *A61B 2017/320094* (2017.08); *A61B 2017/320095* (2017.08)

(58) Field of Classification Search
CPC .......... A61B 17/285; A61B 17/320092; A61B 17/320093; A61B 17/320094; A61B 17/320095
See application file for complete search history.

(56) References Cited

U.S. PATENT DOCUMENTS

| 6,004,335 | A  | * | 12/1999 | Vaitekunas | ...... A61B 17/07207 606/169 |
| 6,068,647 | A  |   | 5/2000  | Witt et al. | |
| 6,660,017 | B2 |   | 12/2003 | Beaupre | |
| 6,695,840 | B2 | * | 2/2004  | Schulze | ............. A61B 18/1445 606/170 |

(Continued)

OTHER PUBLICATIONS

International Search Report of PCT/US09/52518 dated Oct. 6, 2009.

*Primary Examiner* — Jocelin C Tanner
(74) *Attorney, Agent, or Firm* — Carter, DeLuca & Farrell LLP

(57) ABSTRACT

A method of surgically cutting tissue with an ultrasonic instrument that comprises an ultrasonic waveguide that is movable along a longitudinal extent of the ultrasonic instrument comprises the steps of temporarily compressing tissue between two opposing jaws disposed at a distal end of the ultrasonic instrument, applying a resonant ultrasonic wave to the ultrasonic waveguide, and moving the ultrasonic waveguide in a distal direction along the longitudinal extent to advance the ultrasonic waveguide between at least a portion of the jaws to cut and seal the tissue temporarily secured between the jaws.

20 Claims, 15 Drawing Sheets

(56) References Cited

U.S. PATENT DOCUMENTS

| | | |
|---|---|---|
| 7,232,440 B2 * | 6/2007 | Dumbauld .......... A61B 18/1445 606/51 |
| 7,255,697 B2 | 8/2007 | Dycus et al. |
| 7,744,615 B2 | 6/2010 | Couture |
| 9,980,742 B2 * | 5/2018 | Palmer ................. A61B 17/285 |
| 2001/0025184 A1 | 9/2001 | Messerly |
| 2003/0055417 A1 * | 3/2003 | Truckai .............. A61B 18/1815 606/27 |
| 2003/0114851 A1 | 6/2003 | Truckai et al. |
| 2006/0258954 A1 | 11/2006 | Timberlake et al. |
| 2007/0078459 A1 | 4/2007 | Johnson et al. |

* cited by examiner

MEDICAL ULTRASONIC CAUTERIZATION AND CUTTING DEVICE AND METHOD

CROSS-REFERENCE TO RELATED APPLICATIONS

This application is a continuation of U.S. patent application Ser. No. 14/971,329, filed on Dec. 16, 2015, now U.S. Pat. No. 9,980,742, issued on May 29, 2018, which:
is a continuation of U.S. patent application Ser. No. 12/534,030, filed on Jul. 31, 2009, now U.S. Pat. No. 9,247,953, issued on Feb. 2, 2016 (which application claims priority to U.S. Provisional Application Ser. No. 61/085,688, filed on Aug. 1, 2008),
the entire disclosures of which are all hereby incorporated herein by reference in their entireties.

STATEMENT REGARDING FEDERALLY SPONSORED RESEARCH OR DEVELOPMENT

Not Applicable

FIELD OF THE INVENTION

The present systems and methods lies in the field of surgical devices. The present disclosure relates generally to an ultrasonic cutting device and, more particularly, relates to a surgical cutting device with vessel-grasping jaws and an extendable blade-shaped ultrasonic cutting and cauterizing waveguide.

BACKGROUND OF THE INVENTION

Ultrasonic instruments are effectively used in the treatment of many medical conditions. Cutting instruments that utilize ultrasonic waves employ an ultrasonic transducer to generate vibrations along a longitudinal axis of a cutting blade. By placing a resonant wave along the length of the blade, high-speed longitudinal mechanical movement is produced at the blade's end. These instruments are advantageous because the mechanical vibrations transmitted to the end of the blade are very effective at cutting organic tissue and, simultaneously, at generating heat sufficient to cauterize the tissue. Such instruments are particularly well suited for use in minimally invasive procedures, such as endoscopic or laparoscopic procedures, where the blade is passed through a trocar to reach the surgical site.

Physical limitations of known materials used for ultrasonic generators and waveguides limit the speed and size of waveforms used to produce the ultrasonic movement. These limitations define a finite length at the end of the waveguide, referred to as a "hot spot," that can effectively be used to perform the cutting and hemostasis. Tissue touching the waveguide at a particular distance away from the end of the waveguide (outside the hot spot) may be cut, but will not receive enough movement energy to generate the necessary heat to cause hemostasis. When performing endoscopic or laparoscopic surgery, hemostasis is critical because, where the bleeding is not kept under control, the non-invasive laparoscopy must be abandoned and the patient's body cut open to perform surgery on the otherwise inaccessible bleeding area.

Vessels are of particular import when performing ultrasonic surgery. Once severed, a vessel must be properly sealed to prevent dangerous high-volume blood loss by the patient. Vessels of smaller diameters are able to fall entirely within the hot spot of an ultrasonic cutting blade, resulting in a precise cut and complete sealing of the two open ends of the newly cut vessel. However, larger vessels, such as those with a diameter greater than 7 mm, exceed the width of the hotspot at the end of prior-art blades. This is especially true when the vessel is clamped and flattens out to around 11 mm.

Several devices exist that allow for simultaneous or substantially simultaneous cutting and sealing of large-diameter vessels. One such device 100, shown in FIG. 1, for example, is a bipolar electrocautery vessel sealer that has jaws 102, 104 which clamp across the vessel to be sealed. The clamping approximates the opposing walls of the vessel closely, providing a coaptive force. An open slot 106 runs down the middle of the jaws 102, 104 allowing a knife 108 to translate from the proximal end 110 of the jaws 102, 104 to the distal end 112 of the jaws 102, 104. The sealing process is as follows: The jaws 102, 104 are clamped across the vessel to be sealed. Bipolar (each of the jaws is a pole) electrocautery energy is applied to the clamped area of tissue. The energy heats and cauterizes the tissue causing it to become sealed together through the coaptive clamping forces of the jaws. Once the energy has been applied, the knife 108 is translated through the slot 106 in the middle of the jaws 102, 104 thus dividing the sealed vessel in the middle of the sealed area.

Another prior-art device for cutting tissue with an ultrasonic cutting blade is shown in FIG. 2. The ultrasonic clamping and cutting device 200 utilizes a clamp 202 having a set of jaws 204, 206 to clamp tissue in a particular area. Once the tissue is compressed to the point that blood can no longer flow into the clamped areas (i.e., hemostasis), ultrasonic movement is applied through a shaft 212 to an ultrasonic cutting blade 208. The blade moves relative to the jaws 204, 206 to pass through the clamped tissue. High-speed "sawing" movement of the blade 208 immediately slices through the tissue. The friction of the high-speed blade 208 is intended to also create frictional heat, which heat causes the tissue on either side of the cut to cauterize.

However, the prior-art instrument shown in FIG. 2 has a significant gap 210 around the cutting blade 208. The gap 210 is necessary in this device to allow the moving blade 208 to slide between the jaws 206. If this device were used on a vessel, it would not provide coaptive forces to opposing walls of the vessel as it translates and cuts. Close coaption of tissue while the ultrasonic energy is applied is critical when sealing a vessel using ultrasonic energy. Without this coaptive force holding the opposing walls of the vessel tightly together during the application of the ultrasonic energy, the opposing walls of the vessel will not seal together. Once the blade 208 cuts through the vessel, the gap 210 allows the vessel to pull away from the blade 208, often before the vessel is heated by the blade 208 and properly sealed. Naturally, as the diameter of the vessel being cut increases, this hemostasis problem is exacerbated.

Therefore, a need exists to overcome the problems associated with the prior art, for example, those discussed above.

Thus, a need exists to overcome the problems with the prior art systems, designs, and processes as discussed above.

SUMMARY OF THE INVENTION

Briefly, in accordance with exemplary embodiments of the present invention, an ultrasonic surgical instrument includes a shaft having a proximal end and a distal end. A lower jaw has a proximal end and a distal end. The distal end of the shaft terminates into the proximal end of the lower jaw and the lower jaw has an internal trough running from and through the proximal end and terminating at a point prior to the distal end of the lower jaw, an upper surface, and a plurality of teeth disposed on the upper surface of the lower jaw on either side of the trough and at the distal end of the lower jaw. The instrument also includes a pivotable upper jaw with a lower surface facing the upper surface of the lower jaw and a plurality of teeth disposed on the lower surface. The instrument further includes an ultrasonic waveguide extending in a direction through the shaft and into the trough. The waveguide has a blade with a distal end, a proximal end, and a tissue compressing and cutting surface upwardly sloping from the distal end of the blade to the proximal end of the blade. The jaws are operable to compress tissue therebetween and the blade is operable to slide within the trough to further compress and, then, cut the compressed tissue as the blade moves from the proximal end of the lower jaw to the distal end of the lower jaw.

In accordance with a further feature of the invention, a sheath surrounds the waveguide, the first jaw has a first pivot and second jaw has a second pivot and the sheath is coupled to either the first pivot or the second pivot and is operable to move relative to the waveguide and cause the second jaw to move relative to the first jaw.

In accordance with an added feature of the invention, the shaft, the first jaw, the second jaw, and the ultrasonic waveguide form a translating ultrasonic vessel sealer.

In accordance with an additional feature of the invention, there is provided a ramp in the second jaw and a first protrusion extending from the waveguide, the first protrusion sized to engage with the ramp and place a closing force on the second jaw.

In accordance with yet another feature of the invention, there is provided a flat portion at an end of the ramp, the flat portion being substantially parallel to a longitudinal axis of the waveguide when the second jaw is in a closed position.

In accordance with yet a further feature of the invention, the first protrusion has an I-beam shape.

In accordance with yet an added feature of the invention, there is provided a second protrusion extending from the waveguide on a side opposite the first protrusion.

In accordance with yet an additional feature of the invention at least one of the first jaw and the second jaw is biased to an open position.

With the objects of the invention in view, there is also provided an ultrasonic surgical instrument having a shaft having a proximal end and a distal end. An upper jaw and a lower jaw each have a proximal end and a distal end with the distal end of the shaft terminating at the proximal end of the upper and lower jaws. Either the upper jaw or the lower jaw are pivotable and at least one of the jaws has an internal trough running from and through the proximal end of the jaw and terminates at a point prior to the distal end of the jaw. An ultrasonic waveguide extends in a direction through the shaft and into the trough and has a blade, where the blade has a distal end, a proximal end, a top surface portion, and a tissue compressing surface upwardly sloping from the distal end of the blade toward the proximal end of the blade, at least one of the tissue compressing surface and the top surface portion form a cutting surface wherein the jaws are operable to compress tissue therebetween and the blade is operable to slide within the trough to further compress, seal, and cut the compressed tissue as the blade moves in a direction from the proximal end of the jaw to the distal end of the jaw.

With the objects of the invention in view, there is also provided a method for performing a surgical procedure, which includes the steps of providing a shaft having a proximal end and a distal end, providing a first jaw having a proximal end and a distal end, the distal end of the shaft terminating at the proximal end of the first jaw, the first jaw having an internal trough running from and through the proximal end of the first jaw and terminating at a point prior to the distal end of the first jaw and a surface having a plurality of teeth on either side of the trough and at the distal end of the first jaw. The method further includes providing a second jaw having a surface facing the surface of the first jaw and having a plurality of teeth thereat and providing an ultrasonic waveguide extending beyond the shaft and being slidably engagable with the trough, the ultrasonic waveguide having a distal end, a proximal end, a top surface portion, and a tissue compressing surface upwardly sloping from the distal end of the ultrasonic waveguide toward the proximal end of the ultrasonic waveguide, at least one of the tissue compressing surface and the top surface portion forming a cutting surface. The method also includes the steps of compressing tissue between the jaws, applying an ultrasonic wave to the ultrasonic waveguide, and sliding the ultrasonic waveguide within the trough in a direction from the proximal end of the lower jaw to the distal end of the lower jaw to further compress and cut the compressed tissue.

With the objects of the invention in view, there is also provided an ultrasonic surgical instrument includes a shaft, a first jaw having a proximal end at the distal end of the shaft, a second jaw and an ultrasonic waveguide. The first jaw has an internal trough running through the proximal end of the first jaw and a surface on either side of the trough. The second jaw has a surface facing the surface of the first jaw. The waveguide extends beyond the shaft and slidably engages the trough and has a blade with a tissue compressing surface upwardly sloping proximally from a distal end thereof the blade and having an upper portion and a substantially horizontal top surface portion at the upper portion. The tissue compressing surface and/or the top surface portion forms a cutting surface. When the jaws compress tissue therebetween, the blade slides within the trough to further compress and cut the compressed tissue as the blade moves distally.

With the foregoing and other objects in view, there is provided, a method of surgically cutting tissue with an ultrasonic instrument that comprises an ultrasonic waveguide that is movable along a longitudinal extent of the ultrasonic instrument comprising the steps of compressing tissue between two opposing jaws disposed at a distal end of the ultrasonic instrument, applying a resonant ultrasonic wave to the ultrasonic waveguide, and moving the ultrasonic waveguide in a distal direction along the longitudinal extent to advance the ultrasonic waveguide between at least a portion of the jaws to cut and seal the tissue temporarily secured between the jaws.

With the objects in view, there is also provided a method of surgically cutting tissue with an ultrasonic instrument that comprises an ultrasonic waveguide that is movable along a longitudinal extent of the ultrasonic instrument comprises the steps of applying a resonant ultrasonic wave to the ultrasonic waveguide and moving the ultrasonic waveguide in a distal direction to convert two opposing jaws disposed at a distal end of the ultrasonic instrument from an open position to a closed position to compress tissue between the jaws and to advance the ultrasonic waveguide between at least a portion of the closed jaws to cut and seal the tissue compressed between the jaws.

In accordance with another mode, the ultrasonic instrument comprises a hollow shaft having an internal lumen that defines a longitudinal axis and the ultrasonic waveguide is slidably disposed within the internal lumen of the shaft and is advanceable in the distal direction and retractable in a proximal direction parallel to the longitudinal axis.

In accordance with a further mode, the shaft has a proximal end and the ultrasonic instrument further comprises a handle body at the proximal end of the shaft, the handle body comprising a movement mechanism configured to advance and retract the ultrasonic waveguide along the longitudinal extent of the ultrasonic instrument.

In accordance with an added mode, the two opposing jaws comprise a first jaw fixed parallel to the longitudinal axis and a second jaw pivotally connected to the shaft and movable between open and closed positions with respect to the first jaw such that compressing the tissue between the two opposing jaws comprises pivoting the second jaw towards the first jaw to move from the open position to the closed position.

In accordance with an additional mode, the first jaw is one of fixedly connected to the shaft and integral with the shaft.

In accordance with yet another mode, the ultrasonic waveguide has a distal blade, the first jaw has a distal end defining a trough partially exposing the lumen to the environment, and which further comprises advancing the ultrasonic waveguide between at least a portion of the two opposing jaws extends the distal blade into the trough.

In accordance with yet a further mode, the distal blade has proximal and distal ends, a tissue compressing surface sloping upwardly from the distal end of the blade towards the proximal end of the blade and having an upper portion, and a substantially horizontal top surface at the upper portion, at least one of the tissue compressing surface and the top surface forming a cutting surface, and, responsive to the compressing of the tissue between the two opposing jaws and the advancing of the ultrasonic waveguide between at least a portion of the jaws and into the trough, the distal blade further compresses and cuts the compressed tissue.

In accordance with yet an added mode, the second jaw is connected to the shaft by at least one pivot and the ultrasonic instrument further comprises a sheath surrounding the shaft and operatively connected to the at least one pivot, the sheath being configured to move relative to the shaft in the distal direction to cause the second jaw to move about the pivot towards the first jaw to assume the closed position.

In accordance with yet an additional mode, the movement mechanism of the handle body comprises a trigger assembly operatively connected to the ultrasonic waveguide.

In accordance with again another mode, the handle body further comprises an ultrasonic transducer operatively coupled to the ultrasonic waveguide to impart the resonant wave to the waveguide when activated and a battery configured to activate the ultrasonic transducer.

In accordance with again a further mode, the two opposing jaws comprise a first jaw fixed parallel to the longitudinal axis and a second jaw pivotally connected to the shaft and movable with respect to the first jaw such that converting the jaws from the open position to the closed position comprises pivoting the second jaw towards the first jaw.

In accordance with again an added mode, the second jaw has a ramp therein and the ultrasonic waveguide has an upwardly-extending protrusion that is sized to engage with the ramp and place a closing force on the second jaw as the ultrasonic waveguide moves in the distal direction.

In accordance with again an additional mode, the protrusion has an I-beam shape.

In accordance with a concomitant mode, the movement mechanism of the handle body comprises a trigger assembly operatively connected to the ultrasonic waveguide.

Although the systems and methods are illustrated and described herein as embodied in a medical ultrasonic cauterization and cutting device and method, it is, nevertheless, not intended to be limited to the details shown because various modifications and structural changes may be made therein without departing from the spirit of the invention and within the scope and range of equivalents of the claims. Additionally, well-known elements of exemplary embodiments will not be described in detail or will be omitted so as not to obscure the relevant details of the systems and methods.

Additional advantages and other features characteristic of the systems and methods will be set forth in the detailed description that follows and may be apparent from the detailed description or may be learned by practice of exemplary embodiments. Still other advantages of the systems and methods may be realized by any of the instrumentalities, methods, or combinations particularly pointed out in the claims.

Other features that are considered as characteristic for the systems and methods are set forth in the appended claims. As required, detailed embodiments of the systems and methods are disclosed herein; however, it is to be understood that the disclosed embodiments are merely exemplary of the systems and methods, which can be embodied in various forms. Therefore, specific structural and functional details disclosed herein are not to be interpreted as limiting, but merely as a basis for the claims and as a representative basis for teaching one of ordinary skill in the art to variously employ the systems and methods in virtually any appropriately detailed structure. Further, the terms and phrases used herein are not intended to be limiting; but rather, to provide an understandable description of the systems and methods. While the specification concludes with claims defining the systems and methods of the invention that are regarded as novel, it is believed that the systems and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the systems and methods. Advantages of embodiments of the systems and methods will be apparent from the following detailed description of the exemplary embodiments thereof, which description should be considered in conjunction with the accompanying drawings in which.

DETAILED DESCRIPTION OF THE EMBODIMENTS

Figure 1:
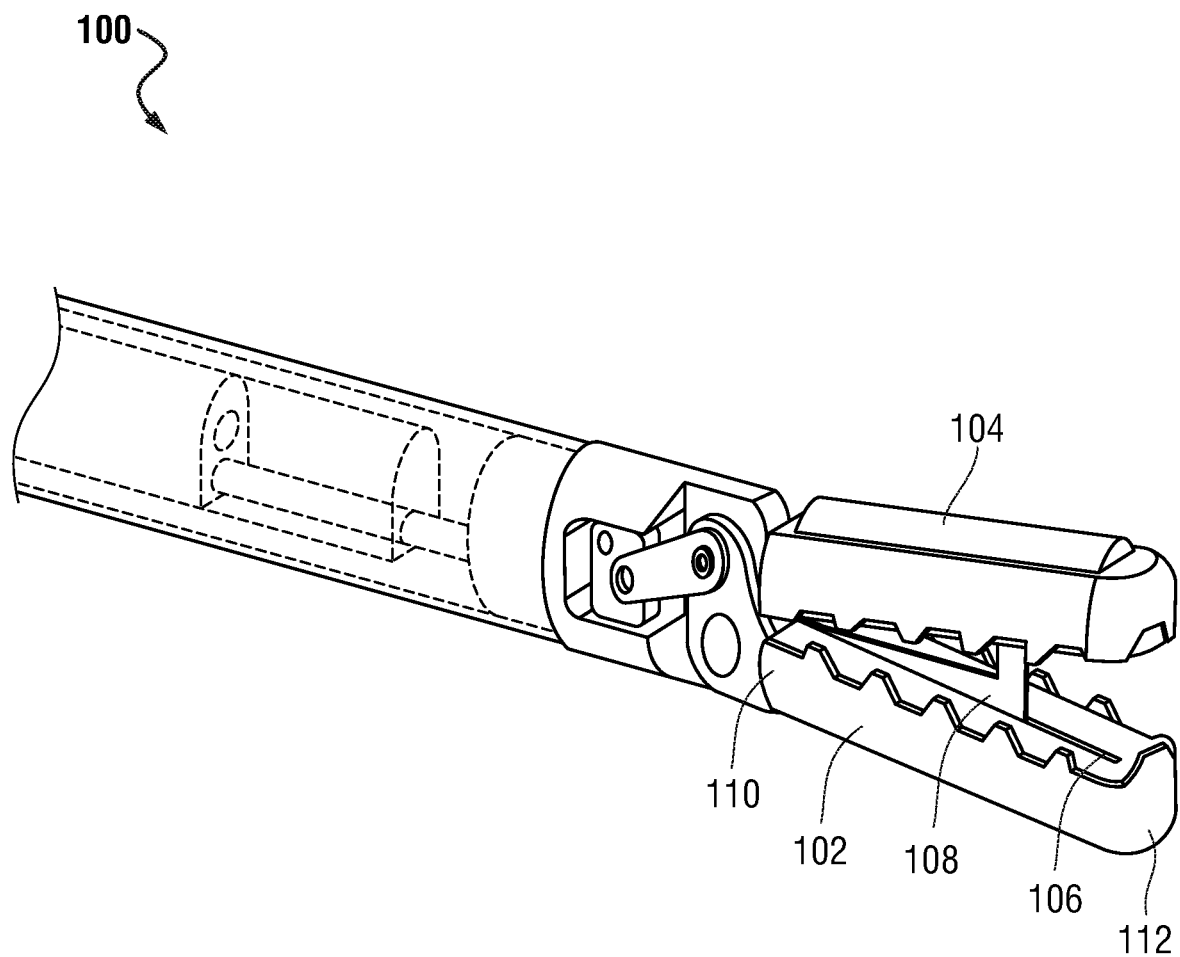
FIG. 1 is a fragmentary, perspective view of a prior-art surgical stapler-cutter.
Figure 2:
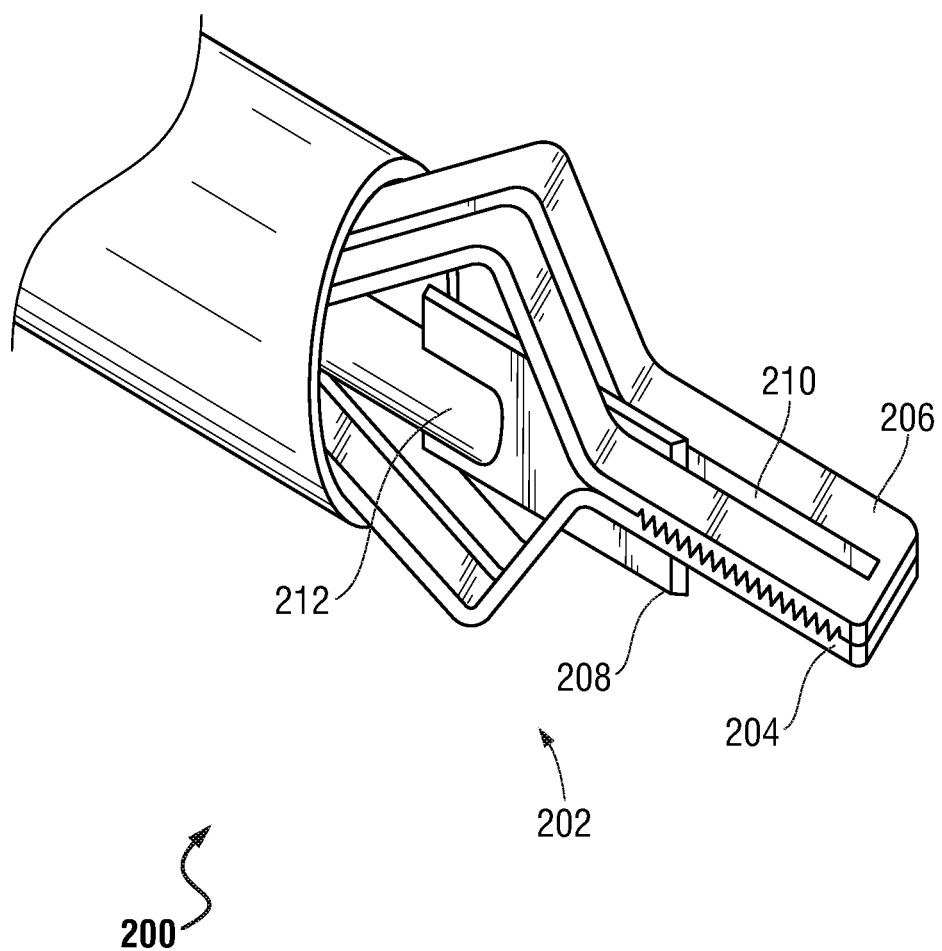
FIG. 2 is a fragmentary, perspective view of a prior-art ultrasonic cutting device.

As required, detailed embodiments of the systems and methods are disclosed herein; however, it is to be understood that the disclosed embodiments are merely exemplary of the systems and methods, which can be embodied in various forms. Therefore, specific structural and functional details disclosed herein are not to be interpreted as limiting, but merely as a basis for the claims and as a representative basis for teaching one skilled in the art to variously employ the systems and methods in virtually any appropriately detailed structure. Further, the terms and phrases used herein are not intended to be limiting; but rather, to provide an understandable description of the systems and methods. While the specification concludes with claims defining the features of the systems and methods that are regarded as novel, it is believed that the systems and methods will be better understood from a consideration of the following description in conjunction with the drawing figures, in which like reference numerals are carried forward.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Alternate embodiments may be devised without departing from the spirit or the scope of the invention. Additionally, well-known elements of exemplary embodiments of the systems and methods will not be described in detail or will be omitted so as not to obscure the relevant details of the systems and methods.

Before the systems and methods are disclosed and described, it is to be understood that the terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact (e.g., directly coupled). However, "coupled" may also mean that two or more elements are not in direct contact with each other, but yet still cooperate or interact with each other (e.g., indirectly coupled).

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, and top/bottom. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

It will be appreciated that embodiments of the systems and methods described herein may be comprised of one or more conventional processors and unique stored program instructions that control the one or more processors to implement, in conjunction with certain non-processor circuits and other elements, some, most, or all of the functions of the devices and methods described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs) or field-programmable gate arrays (FPGA), in which each function or some combinations of certain of the functions are implemented as custom logic. Of course, a combination of these approaches could also be used. Thus, methods and means for these functions have been described herein.

The terms "program," "software," "software application," and the like as used herein, are defined as a sequence of instructions designed for execution on a computer system or programmable device. A "program," "software," "application," "computer program," or "software application" may include a subroutine, a function, a procedure, an object method, an object implementation, an executable application, an applet, a servlet, a source code, an object code, any computer language logic, a shared library/dynamic load library and/or other sequence of instructions designed for execution on a computer system.

Herein various embodiments of the systems and methods are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

The present invention, according to one embodiment, overcomes problems with the prior art by providing a surgical device that is able to clamp onto tissue, such as large vessels, to slide a tapered ultrasonic cutting blade within the clamped area of the tissue, thereby providing the critical coaptive force to opposing vessel walls during the sealing and to ultrasonically cauterizing and sealing the clamped tissue as it is cut.

Ultrasonic Surgical Device

Figure 3:
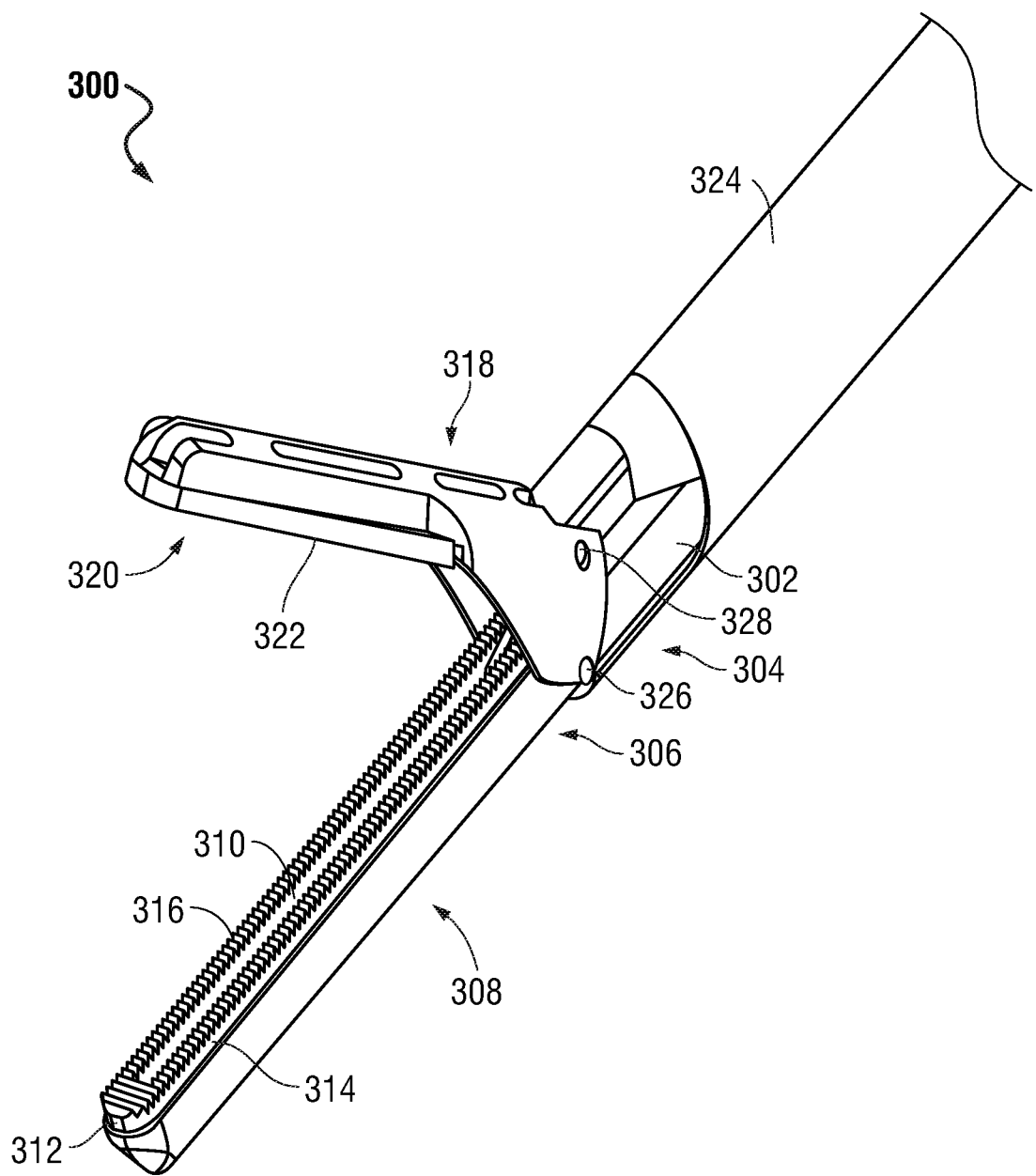
FIG. 3 is a fragmentary, perspective view of an ultrasonic cutting and cauterizing device in accordance with an exemplary embodiment of the present invention with the jaws in an open position and a waveguide in a retracted position within a trough in a lower jaw.

Described now is an exemplary ultrasonic surgical instrument according to one embodiment of the present invention. Referring to FIG. 3, the instrument 300 is shown in a perspective view. The instrument 300 includes a shaft 302 with a proximal end (out of view in this diagram) and a distal end 304. The distal end 304 terminates into the proximal end 306 of a lower jaw 308. The lower jaw 308 defines an internal trough 310 running from and through the proximal end 306 of the lower jaw 308 to a point just before the lower jaw's distal extent 312. The lower jaw 308 also includes an upper surface 314 with a plurality of teeth 316 disposed on either side of the trough 310 and at the distal end 312 of the lower jaw 308.

The instrument 300 also has a pivoting upper jaw 318 with a lower surface 320 facing or opposing the upper surface 314 of the lower jaw 308. A second plurality of teeth 322 is disposed on the lower surface 320 of the upper jaw 318. The upper 318 and lower 308 jaws are operable to compress tissue therebetween. The teeth 316, 322, in one exemplary embodiment, are ridges that help grip the tissue and prevent it from sliding out from between the closed jaws 308 and 318.

Figure 4:
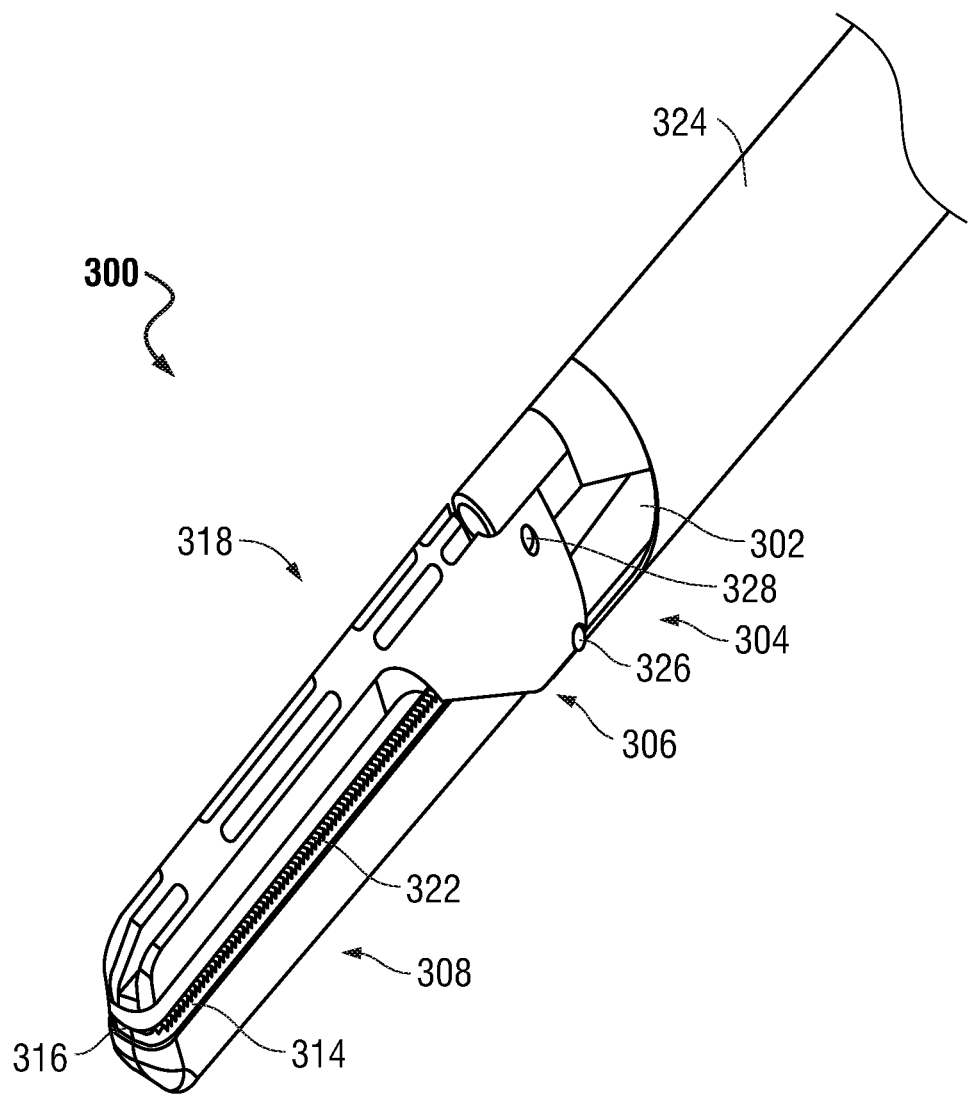
FIG. 4 is a fragmentary, perspective view of the ultrasonic cutting and cauterizing device of FIG. 3 with the jaws in a clamping position and the waveguide in an extended position.

In one embodiment of the present invention, the pivotable upper jaw 318 is actuated/activated by a sheath 324 that surrounds and moves relative to the shaft 302. In the embodiment shown in FIG. 3, the pivoting upper jaw 318 is attached to the shaft 302 at a first point 326 and is attached to the sheath 324 at a second point 328. When the sheath 324 is pushed toward the distal end 304 of the shaft 302, the upper jaw 318 pivots around both attachment points 326 and 328 and, as shown in FIG. 4, moves toward the lower jaw 308. The position shown in FIG. 4 is a fully clamped position of the jaws 308, 318. Of course, the sheath 324 is not the only configuration for operating the upper jaw 318. Any mechanical means of moving one of the jaws 308 and 318 relative to the other so that tissue is clamped there between is within the spirit and scope of the present invention. In addition, the shaft 302 and the lower jaw 308 are not necessarily two separate elements and can be, instead, one continuous piece of material. For example, the sheath 324 can be a hollow body defining two lumens therein, one for the shaft 302 and one for a non-illustrated actuation rod. That actuation rod can exist within the second lumen and distal translation can cause closure of the upper jaw 318.

Figure 5:
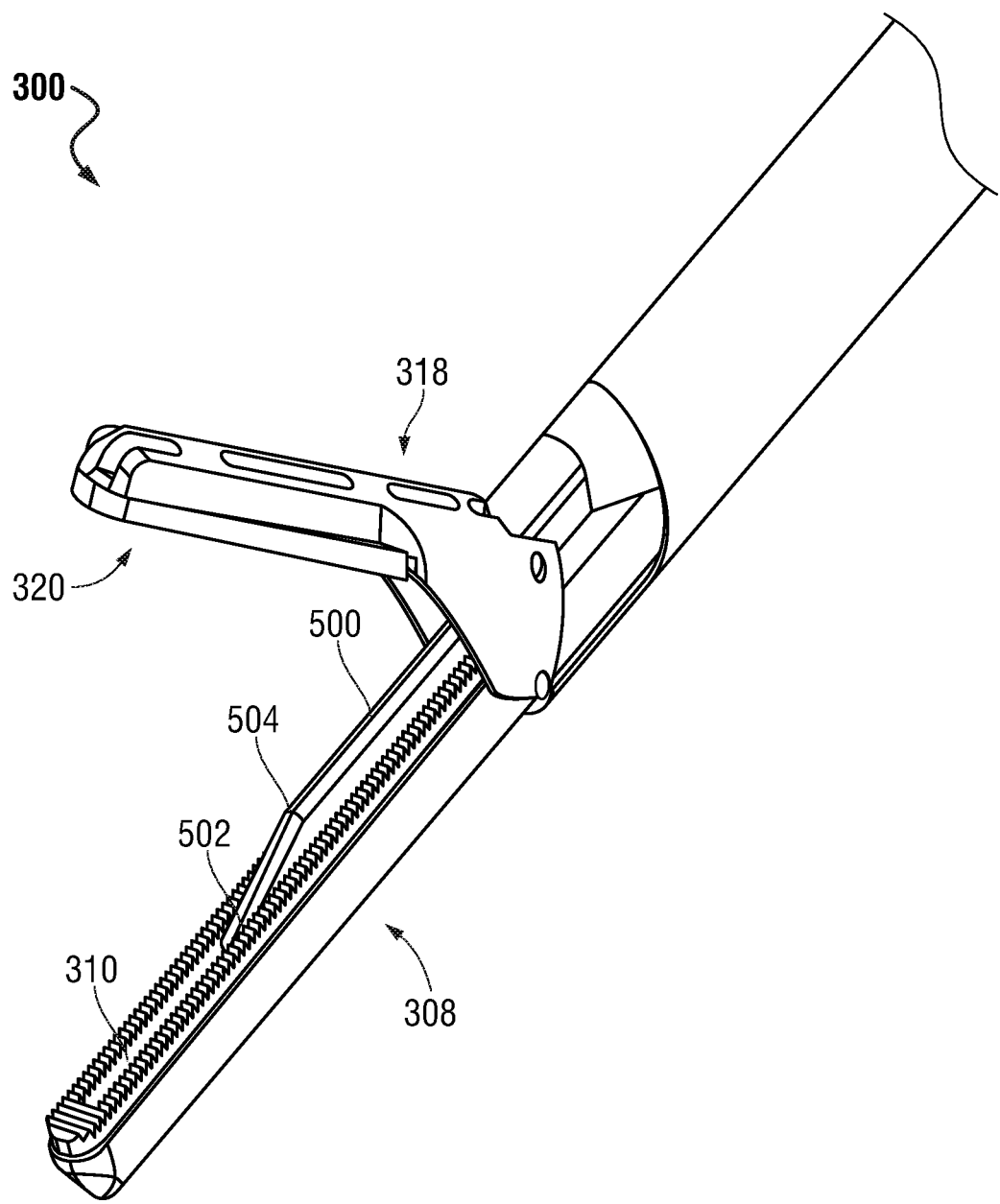
FIG. 5 is a perspective view of the ultrasonic cutting and cauterizing device of FIG. 3 with the jaws in an open position and the waveguide in an intermediate position.
Figure 6:
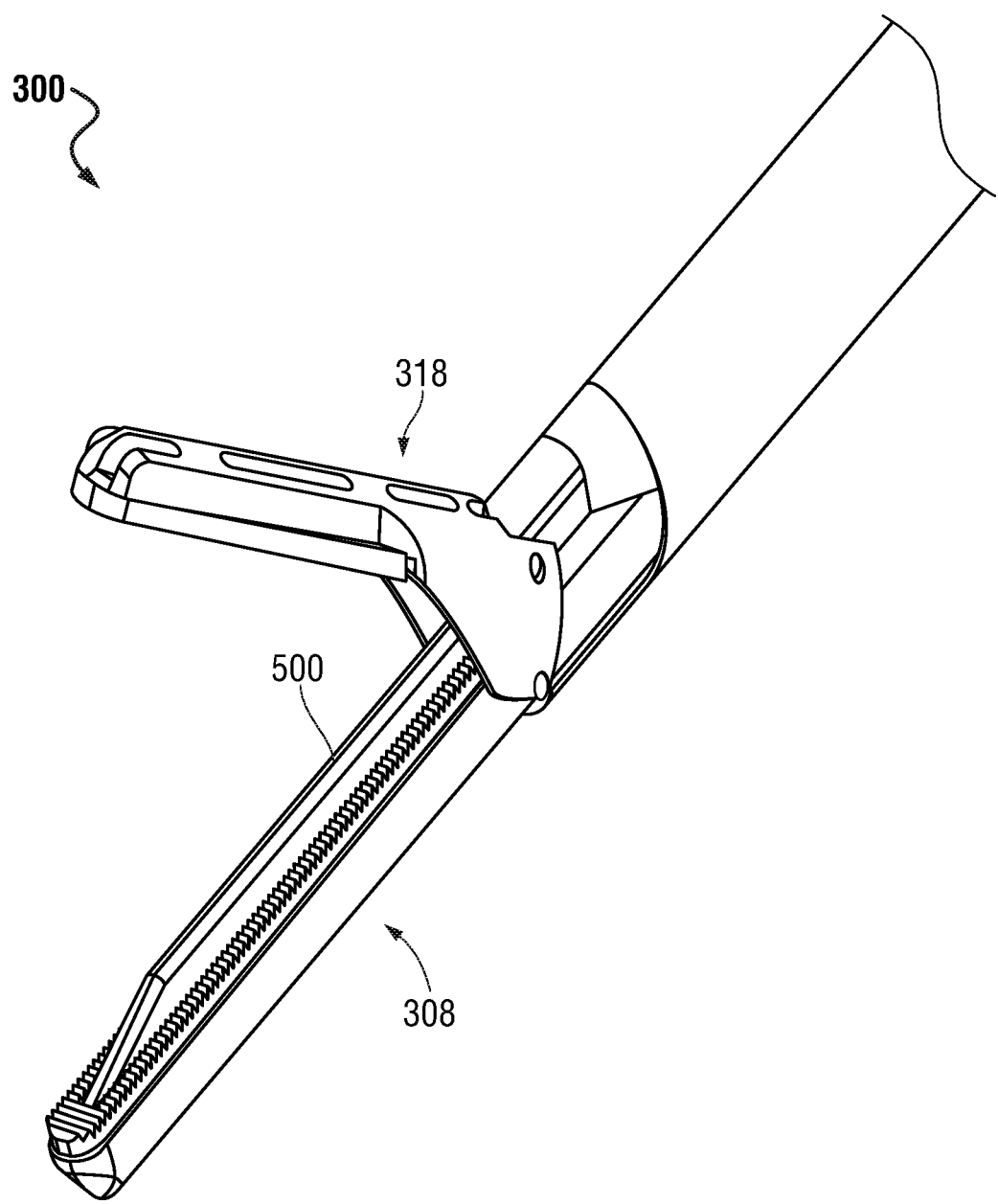
FIG. 6 is a perspective view of the ultrasonic cutting and cauterizing device of FIG. 3 with the jaws in an open position and the waveguide in a fully extended position.

Referring now to FIG. 5, an inventive sliding ultrasonic waveguide 500 is shown within the trough 310. According to embodiments of the present invention, the waveguide 500 is able to be moved from a retracted or withdrawn position, shown in FIG. 3 through any intermediate position (e.g., shown in FIG. 5) to, as will be explained in detail below, a fully extended position shown in FIGS. 4 and 6.

Figure 7:
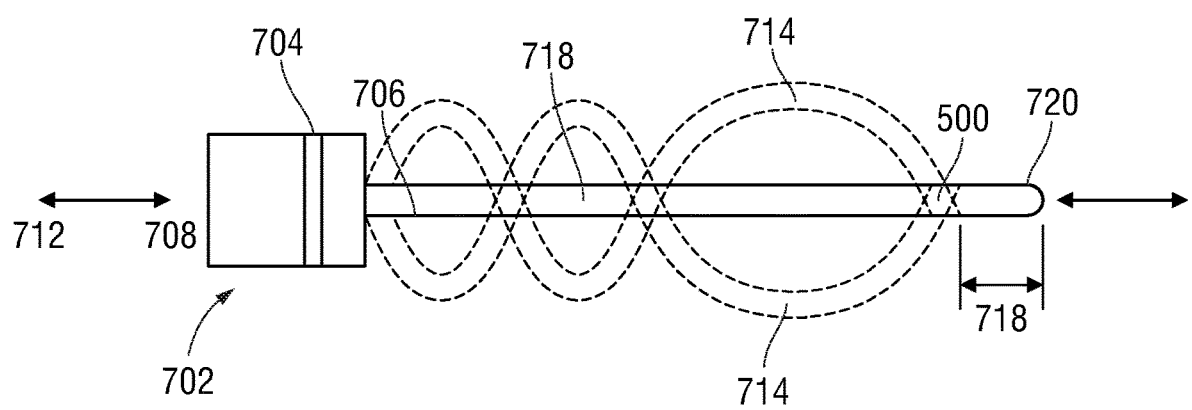
FIG. 7 is a diagrammatic illustration of the effect that a resonant driving wave input to a transducer has on a waveguide of the ultrasonic cutting device in accordance with an exemplary embodiment of the present invention with an exaggerated sinusoidal pattern shown representing the amplitude of axial motion along the length of the waveguide.

Referring briefly to FIG. 7, an ultrasonic transducer 702 is shown coupled to the waveguide 500. This transducer 702 is an electro-mechanical device that converts electrical signals to physical movement. In a broader sense, a transducer is sometimes defined as any device that converts a signal from one form to another. An analogous transducer device is an audio speaker, which converts electrical voltage variations representing music or speech to mechanical cone vibration. The speaker cone, in turn, vibrates air molecules to create acoustical energy. In the present invention, a driving wave is input to the transducer 702, which then imparts physical movements to the waveguide 500. As will be shown, this movement sets up a resonating wave on the waveguide 500, resulting in motion at the end of the waveguide 500.

Responding to a positive portion of the driving wave, the transducer 702 moves a portion 704 of the transducer 702, which is physically attached to a portion 706 of the attached waveguide 500, in a first direction 708. Likewise, the transducer 702 responds to a negative portion of the driving wave and moves the portion 704 of the transducer 702 in a second direction 712. One exemplary embodiment of the portion 704 is a stack of piezo-electric crystals.

The alternating movement 708, 712 of the transducer portion 704 places an axial compression/expansion wave illustrated by the sinusoidal wave 714 along the length of the waveguide 500. The wave 714 alternatively pulls the end 720 of the waveguide 500 toward the transducer 702 and pushes it away from the transducer 702, thereby longitudinally moving the tip 720 of the waveguide 500 along distance 718. The tip 720 is considered an "anti-node," as it is a moving point of the sine wave 714. The resulting movement of the waveguide 500 produces a "sawing" movement along distance 718 at the end of the waveguide 500. (The wave 714 and linear movement along distance 718 are greatly exaggerated in FIG. 7 for ease of discussion.) This high-speed movement along distance 718, as is known in the art, provides a cutting waveguide that is able to slice easily through many materials, such as tissue and bone. The waveguide 500 also generates a great deal of frictional heat when so stimulated, which heat is conducted within the tissue that the waveguide 500 is cutting. This heat is sufficient to cauterize blood vessels within the tissue being cut.

Returning now to FIG. 5, the waveguide 500 is shown having an upwardly sloping surface 502 and substantially horizontal surface 504 at an upper portion of the upwardly sloping surface 502. The upwardly sloping surface 502 further compresses tissue when the tissue is already compressed between the jaws 308, 318. Any sub-portion(s) of the surfaces 502, 504 can be the ultrasonic cutting/cautery surface and a frequency of the driving wave will determine the length of such a cutting/cautery surface (increasing the frequency decreases this length and decreasing the frequency increases the length). In one exemplary embodiment, only the upwardly sloping surface 502 comprises the cutting/cautery surface. In another exemplary embodiment, both the upwardly sloping surface 502 and a portion of the substantially horizontal surface 504 comprises the cutting/cautery surface. If desired, the substantially horizontal surface 504 can slope upward like the surface 502 but at an angle, e.g., of about 3-5 degrees.

In FIG. 5, the jaws 308 and 318 are shown in an open position only for the purpose of illustrating the blade 500 within the trough 310. In actual operation, the jaws 308 and 318 will not be in the open position, but will, instead, be in the closed position shown in FIG. 4.

The device 300 operates as set forth in the following text. When the waveguide 500 is in the retracted position, shown in FIG. 3, the device 300 is positioned to insert tissue between the jaws 308, 318. The sheath 324 is, then, slid forward relative to the shaft 302, causing the jaws 308, 318 to clamp down upon the tissue. Preferably, the clamping force will be sufficient to blanch blood from the clamped area and prevent further blood flow to the tissue within the jaws suspended above the trough 310. Next, the ultrasonically-moving waveguide 500 is extended distally along the trough 310. As the waveguide 500 moves distally, the sloped edge 502 of the waveguide 500 forces the tissue up against the bottom surface 320 of the upper jaw 318. This forcing further compresses the tissue. During or after the further compression of the tissue, the cutting area of at least one of the surfaces 502, 504 contacts the tissue and both cuts and cauterizes it. Because the tissue is highly compressed, solid physical contact with the ultrasonically moving waveguide 500, 504 improves heat and movement transferred to the tissue to be cut. Advantageously, because the tissue is compressed by the jaws 308, 318 to such a degree, it does not pull away from the waveguide 500 and remains in place long enough for hemostasis to occur.

Prior art ultrasonic devices had and have fixed-length cutting surfaces. This means that the prior art devices are limited in the size of vessels that can be cut/cauterized. The device 300, in contrast, advantageously allows much larger vessels to be cut and cauterized than any device before, even where the hot spot is smaller than the diameter of the vessel to be cut. Using the illustration of FIGS. 3 and 6, for example, cutting of a vessel having a diameter as long as the exposed portion of the trough 310 in the figures is possible with the device 300. Furthermore these devices are often used for cutting through sections of mesentery that contain large quantities of small blood vessels. Having a large hot spot will allow the surgeon to transect through these areas more rapidly.

Figure 8:
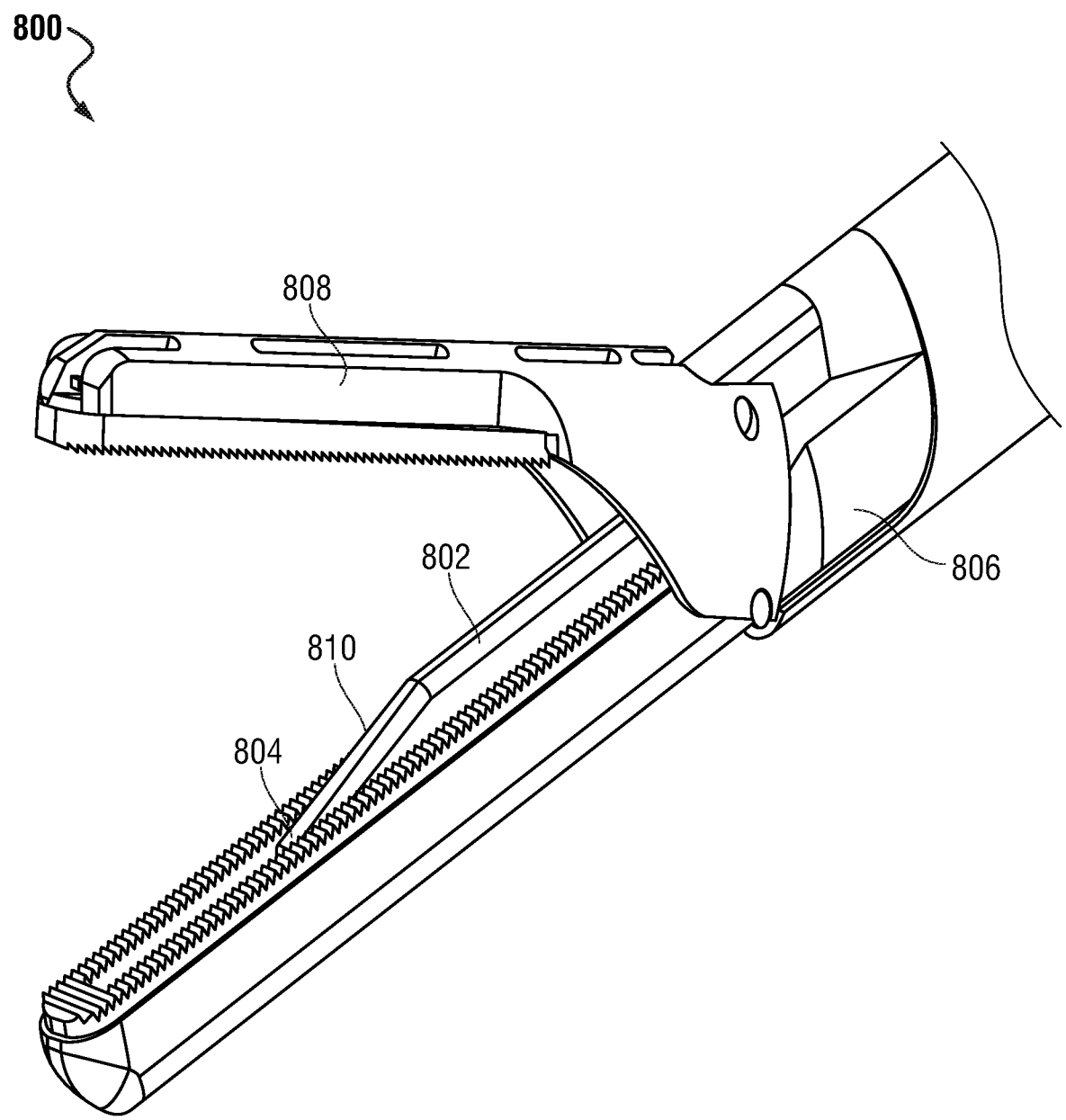
FIG. 8 is a fragmentary, perspective view of the ultrasonic cutting and cauterizing device of FIG. 3 with an alternative waveguide shape in accordance with an exemplary embodiment of the present invention.

FIG. 8 shows an embodiment 800 of the inventive device that utilizes a blade 802 having a novel shape. The blade 802 is provided with a relatively wide angled blade area 804 at the tip of the blade, where initial contact is made with tissue when the blade 802 is ejected out from within the interior of the shaft 806. The angled flat portion 804 of the blade 802 simultaneously pushes or "scoops" the tissue up toward the upper jaw 808 and toward a second area of the blade 810 that, in the embodiment shown in FIG. 8, is shaped to a sharp cutting edge. Once the tissue is pushed beyond the flat area 804, the tissue contacts sharp cutting edge 810 and tissue cutting takes place. Advantageously, by the time the tissue reaches the cutting edge 810, the flat area 804 has placed the tissue under pressure. The pressure ensures sufficient contact between the tissue and the cutting blade 802 to allow cauterization to occur.

Figure 9:
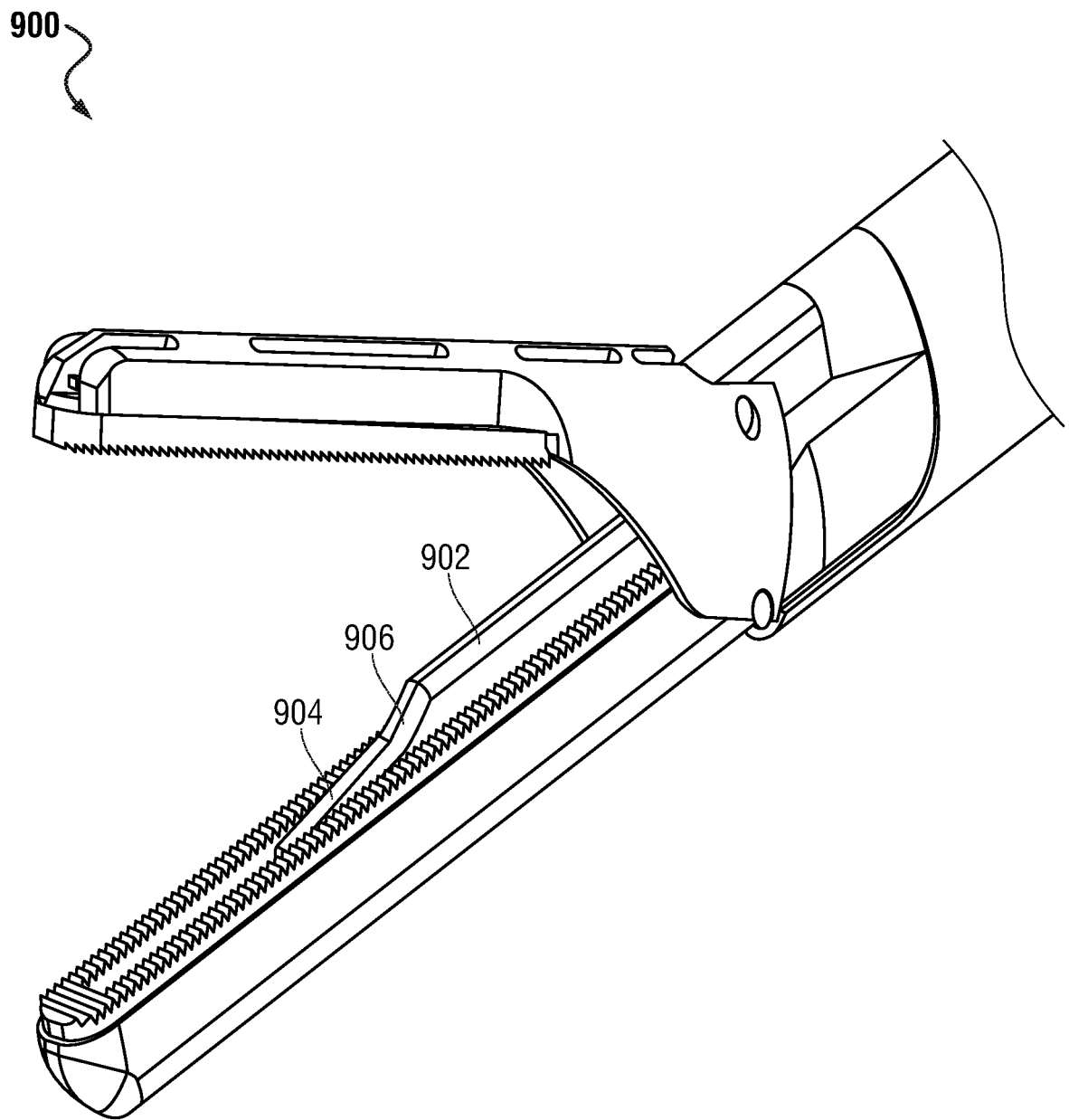
FIG. 9 is a fragmentary, perspective view of the ultrasonic cutting and cauterizing device of FIG. 3 with a second alternative waveguide shape in accordance with an exemplary embodiment of the present invention.

FIG. 9 shows a second embodiment of the surgical cutting device of FIG. 8. In the embodiment 900 of FIG. 9, the cutting blade 902 has a longer, more gradually sloping (from front to back), flat (less sharp), non-cutting portion 904. The non-cutting portion 904 terminates into a cutting portion 906 that is shorter and steeper than the cutting portion 810 of FIG. 8. The shorter, steeper portion 906 provides an added pressurizer of the tissue prior to it moving on to the cutting portion 902. However, cutting may also take place on the steeper portion 906.

FIGS. 5, 8, and 9 and a comparison between them show that the present invention is not limited to any particular geometry or dimensions of cutting blades. Many variations are within the spirit and scope of the present invention.

Figure 10:
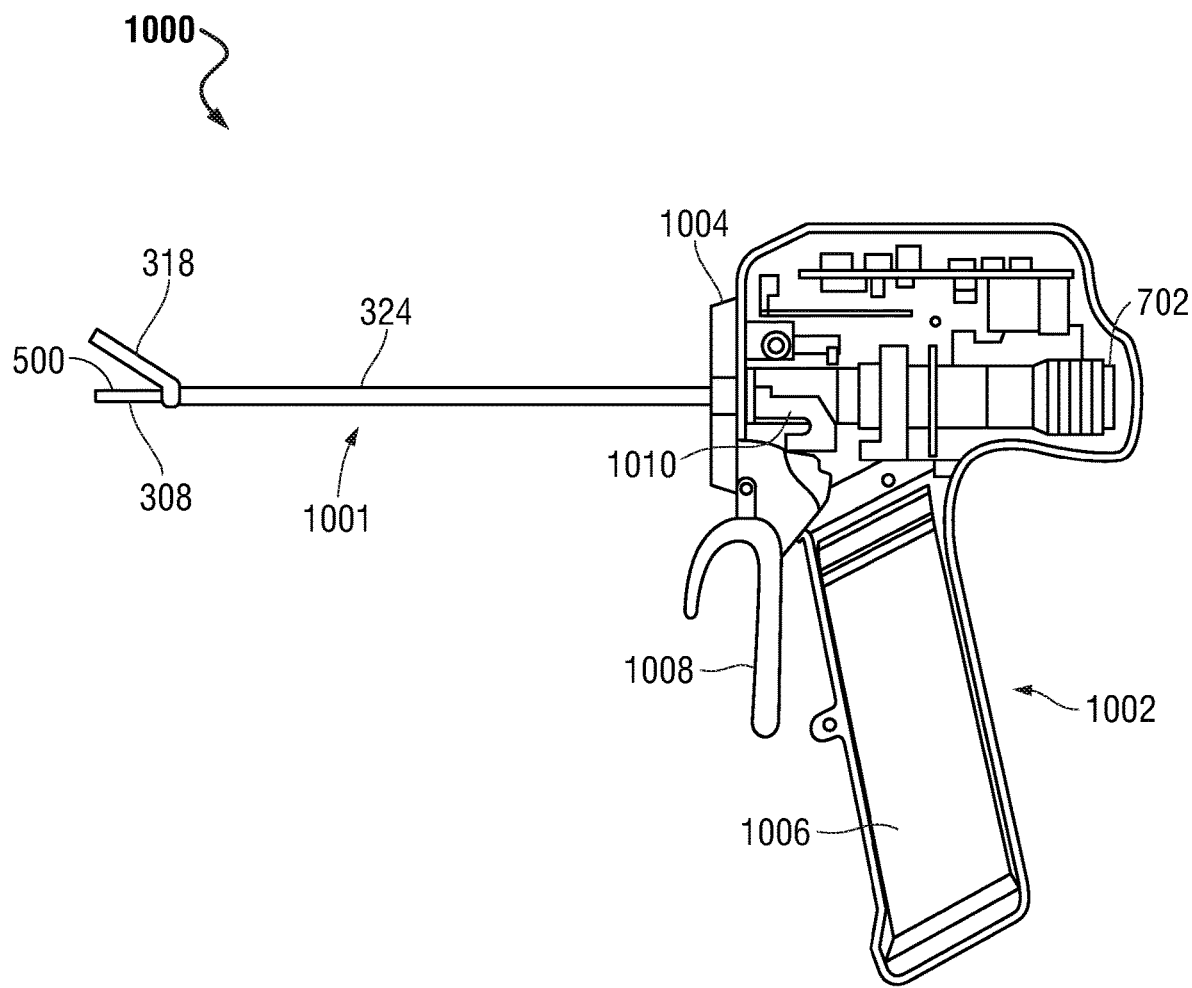
FIG. 10 is an elevational view of a surgical handle attached to an ultrasonic cutting and cauterizing device in accordance with an exemplary embodiment of the present invention.

FIG. 10 shows an exemplary surgical device 1000 utilizing the inventive cutting and cauterizing waveguide assembly, designated with numeral 1001. The surgical device 1000 includes a handle 1002 mechanically coupled to and operable to manipulate the waveguide assembly 1001. The handle 1002 includes the transducer 702 mechanically coupled to the waveguide 500, which generates the ultrasonic cutting and cauterizing motion at the distal end of the waveguide 500. Advantageously, the handle 1002 includes a spindle 1004 that allows the waveguide assembly 1001 and the transducer 702 to rotate relative to the handle 1002, for operation at a variety of angles.

In one exemplary embodiment of the present invention, power is derived from only a battery 1006, or a group of batteries, small enough to fit either within the handle 1002 or within a small non-illustrated box that attaches to the user, for example, at a waistband. State-of-the-art battery technology provides powerful enough batteries of a few centimeters in height and width and a few millimeters in depth to accomplish this task.

The handle 1002 is provided with a trigger 1008 that, when depressed, causes the blade portion of the waveguide 500 to move distally within the trough (not shown in this view) toward a distal end of the jaws 308, 318. In another exemplary embodiment, forward movement speed of the waveguide 500 is limited by a trigger controller 1010, which, in one exemplary embodiment, slows the maximum possible speed of trigger depression as trigger pressure increases. Such a trigger controller 1010 ensures that the speed of the blade remains within a particular range if the surgeon applies force on the trigger 1008 that would cause the blade 500 to move faster than acceptable for proper cutting/cauterizing of tissue. The controller 1010 can be any device that can limit a rate of movement, such as a fly governor or a dashpot, for example. Alternatively the trigger motion could load a constant force spring which would drive the blade with a fixed forward pressure. As a result, the blade will move, but will be limited to a maximum velocity, which will result in proper sealing of the tissue. In such a case, an audible alert would be utilized to notify the surgeon that the transection was complete.

Figure 11:
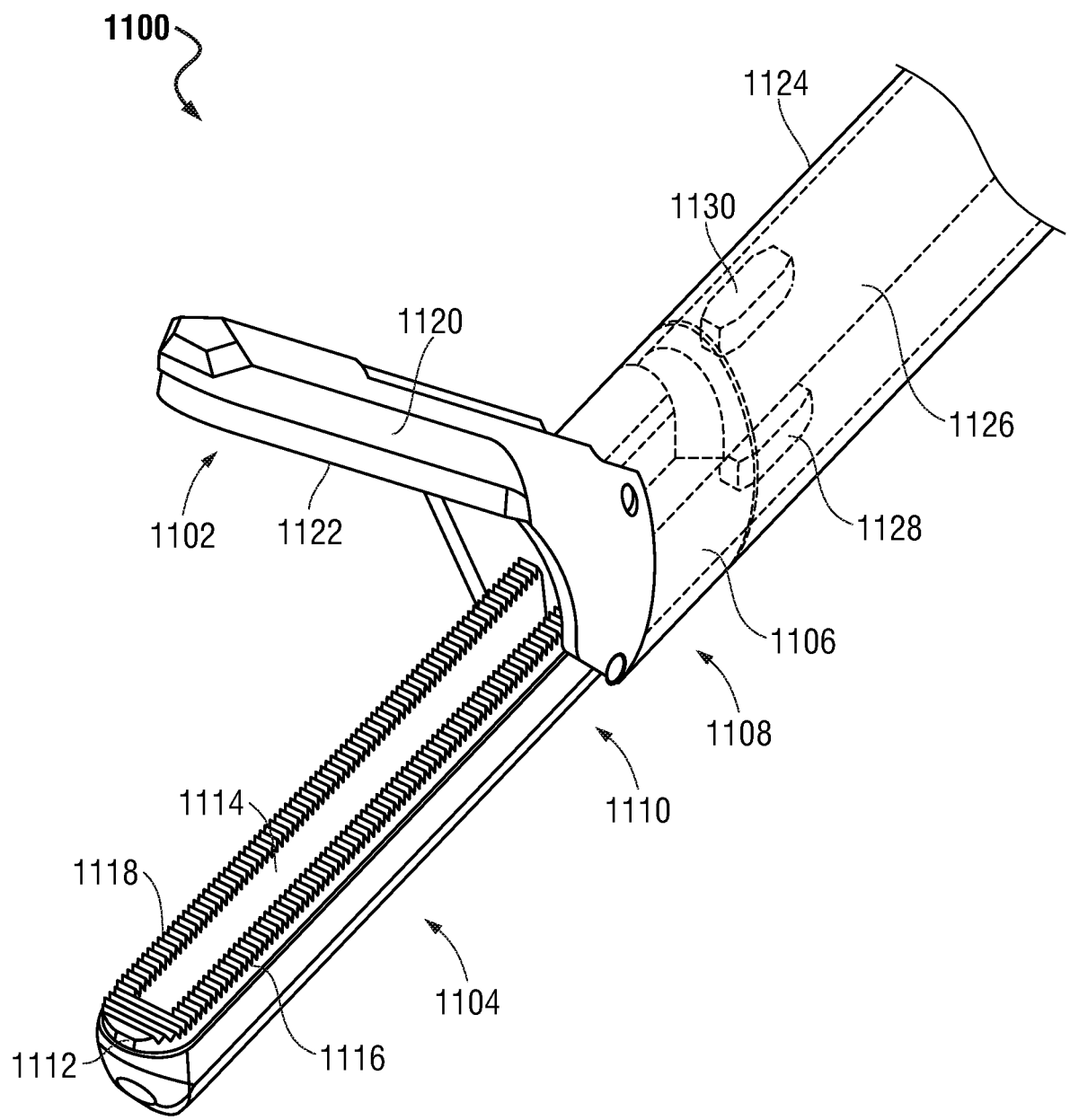
FIG. 11 is a fragmentary, perspective view of an ultrasonic cutting and cauterizing device with an I-beam waveguide in a retracted position in accordance with an exemplary embodiment of the present invention.

FIGS. 11-14 show an embodiment of the present invention that utilizes what is referred to herein as an "I-beam" blade. Turning first to FIG. 11, an ultrasonic surgical cutting and cauterizing assembly 1100 is shown. The assembly 1100 is provided with an upper jaw 1102 and a lower jaw 1104. Although the jaws shown in the instant specification have been shown with and described as having a pivoting upper jaw and stationary lower jaw, the invention is not so limited. In other embodiments, the lower jaw can pivot and the upper jaw is stationary or, alternatively, both jaws are able to pivot. Also included in the assembly 1100 of FIG. 11 is a shaft 1106 having a proximal end (not shown in FIG. 11) and a distal end 1108. The lower jaw 1104 has a proximal end 1110 and a distal end 1112. The distal end 1108 of the shaft 1106 terminates at the proximal end 1110 of the lower jaw 1104. As in the assembly 300, shown in FIGS. 3-6, the lower jaw 1104 has an internal trough 1114 running from and through the proximal end 1110 of the lower jaw 1104 and terminating at a point prior to the distal end 1112 of the lower jaw 1104. The lower jaw 1104 also has an upper surface 1116 that surrounds the trough on three sides and has a plurality of teeth 1118 thereat. The pivotable upper jaw 1102 includes a lower surface 1120 facing the upper surface 1116 of the lower jaw 1104 and has a plurality of teeth 1122 thereat.

The transparent view of the sleeve 1124 and shaft 1106 in FIG. 11 shows an ultrasonic waveguide 1126 present and withdrawn into the shaft 1106. The novel waveguide 1126 features a pair of I-beam-shaped protrusions 1128 and 1130 extending from opposite sides of the waveguide 1126. As will be explained and shown in the following figures, the I-beam-shaped protrusions 1128 and 1130 automatically close the jaws 1102 and 1104 as the waveguide 1126 extends from the shaft 1106. This automatic closing of the jaws 1102 and 1104 advantageously eliminates a step from the cutting and cauterizing process performed with the present invention making surgical processes even easier for the surgeon utilizing the instrument 1100.

Figure 12:
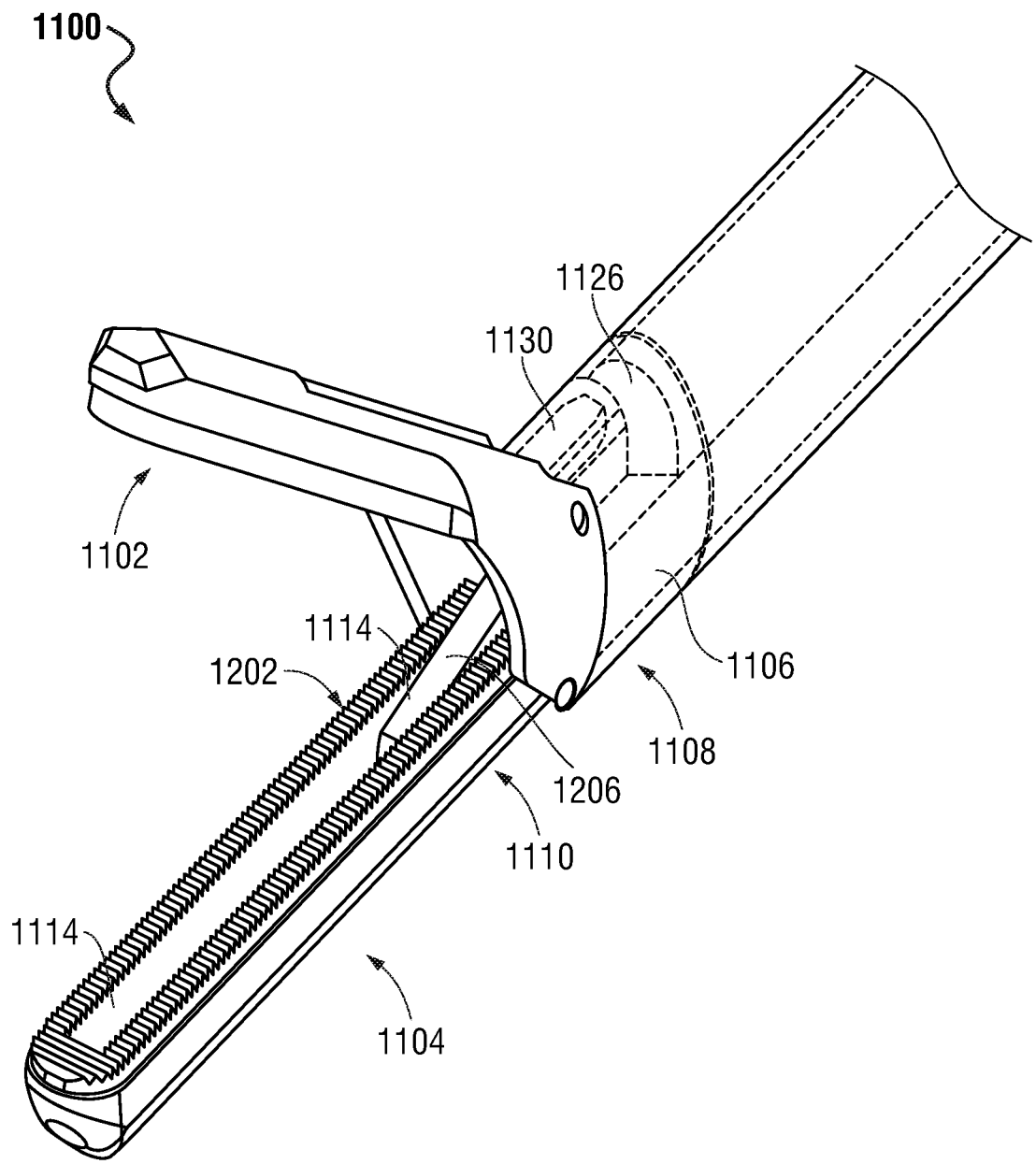
FIG. 12 is a fragmentary, perspective view of the ultrasonic cutting and cauterizing device of FIG. 11 with the jaws in an open position and a waveguide in a partially extended position within a trough in a lower jaw.

FIG. 12 shows a distal end 1202 of the waveguide 1126 extending slightly out of the distal end 1108 of the shaft 1106. The distal end 1202 of the waveguide 1126 features a tissue compressing surface 1204 upwardly sloping from the distal end 1202 of the waveguide 1126 to a proximal end of the waveguide 1126 (not shown in FIG. 12). The tissue compressing surface 1204 terminates into a cutting surface 1206 that is also upwardly sloping from the tissue compressing surface 1204 of the waveguide 1126 to a proximal end of the waveguide 1126 (not shown in FIG. 12).

Figure 13:
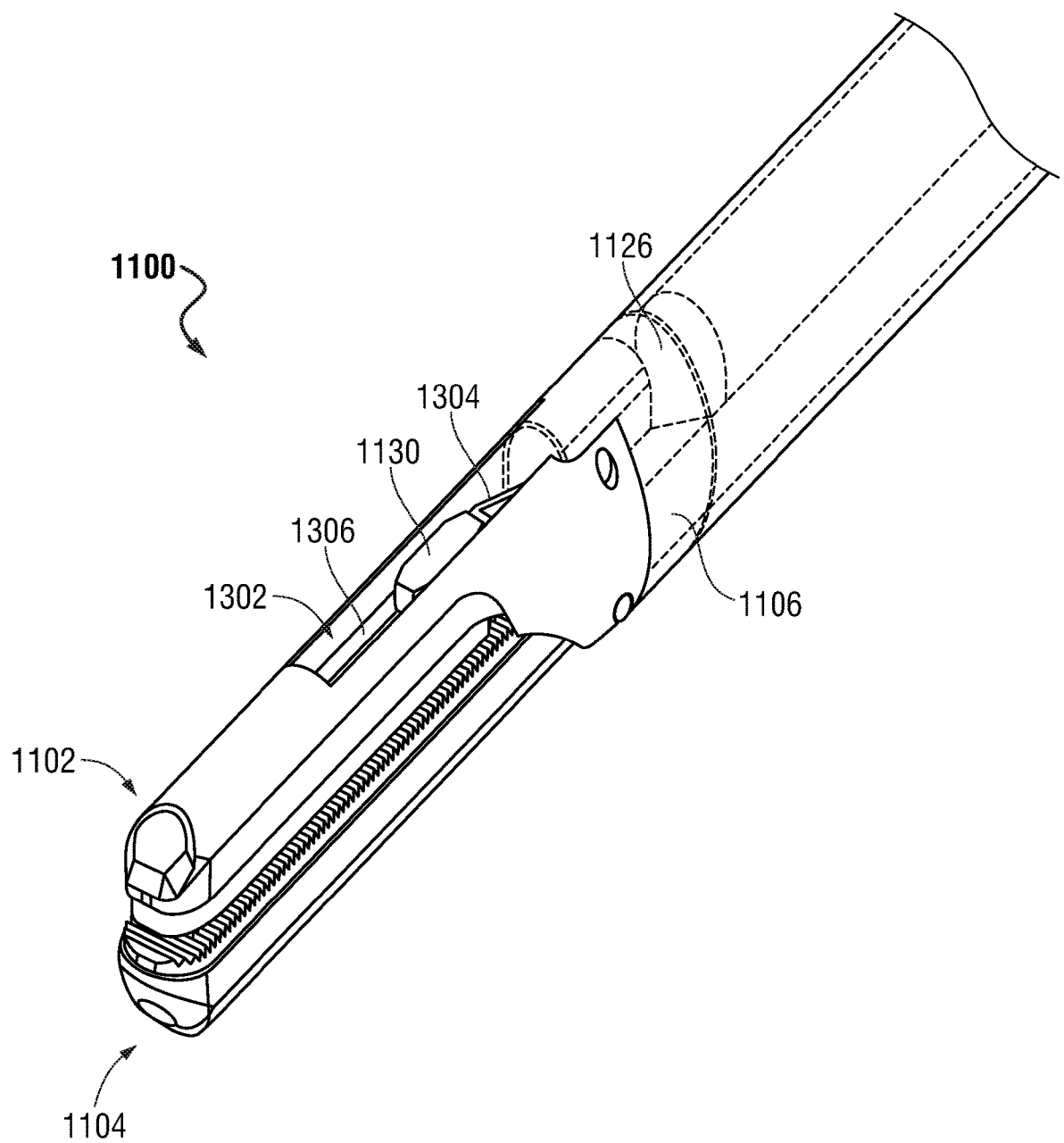
FIG. 13 is a fragmentary, perspective view of the ultrasonic cutting and cauterizing device of FIG. 11 with the jaws in a clamped position and the waveguide in an intermediate position.

FIG. 13 illustrates the functionality of the I-beam protrusions 1128 and 1130. The view of FIG. 13 shows the jaws 1102 and 1104 in a closed or clamped state. The upper jaw 1102 features a recessed area 1302. Within the recessed area 1302 is a ramp 1304, which terminates into a flat area 1306. In their natural state, the jaws 1102 and 1104 are biased to an open position, as shown in FIGS. 11 & 12. As the waveguide 1126 continues to be extended out of the shaft 1106, the upper I-beam protrusion 1130 comes into contact first with the ramp 1304. Although not shown in FIG. 13, the lower jaw 1104 is also provided with a recessed area for engaging the lower I-beam protrusion 1128. The fixed distance between the I-beam protrusions 1128 and 1130 squeezes the jaws 1102 and 1104 together, forcing the upper jaw 1102 to close toward the lower jaw 1104 as the I-beam 1130 is pushed further up the ramp 1304. Once the upper jaw 1102 and lower jaw 1104 are in their fully clamped positions, as shown in FIG. 13, the upper protrusion of the I-beam follows the flat portion 1306 of the recess 1302 of the upper jaw 1102. The jaws 1102 and 1104 cannot become unclamped while the I-beam protrusion is positioned along the flat portion 1306. The I-beam embodiment advantageously results in an automatic clamping of the jaws 1102 and 1104 and extension of the cutting waveguide 1120 within the trough 1114, all in a single step. The operator need only extend the waveguide 1126 to cause the jaws 1102 and 1104 to compress tissue therebetween. The waveguide 1126 continues to slide within the trough 1302 to further compress and cut the compressed tissue as the waveguide 1126 moves in a direction from the proximal end 1110 of the jaws 1102 and 1104 to the distal end 1112 of the jaws 1102 and 1104.

As the waveguide 1126 is retracted back into the shaft 1106, the bias on the jaws 1102 and 1104 forces the jaws 1102 and 1104 to begin opening. Once the I-beam protrusion 1130 is moved beyond the ramp 1304, the jaws 1102 and 1104 return to their fully open position, shown in FIGS. 11 and 12.

Figure 14:
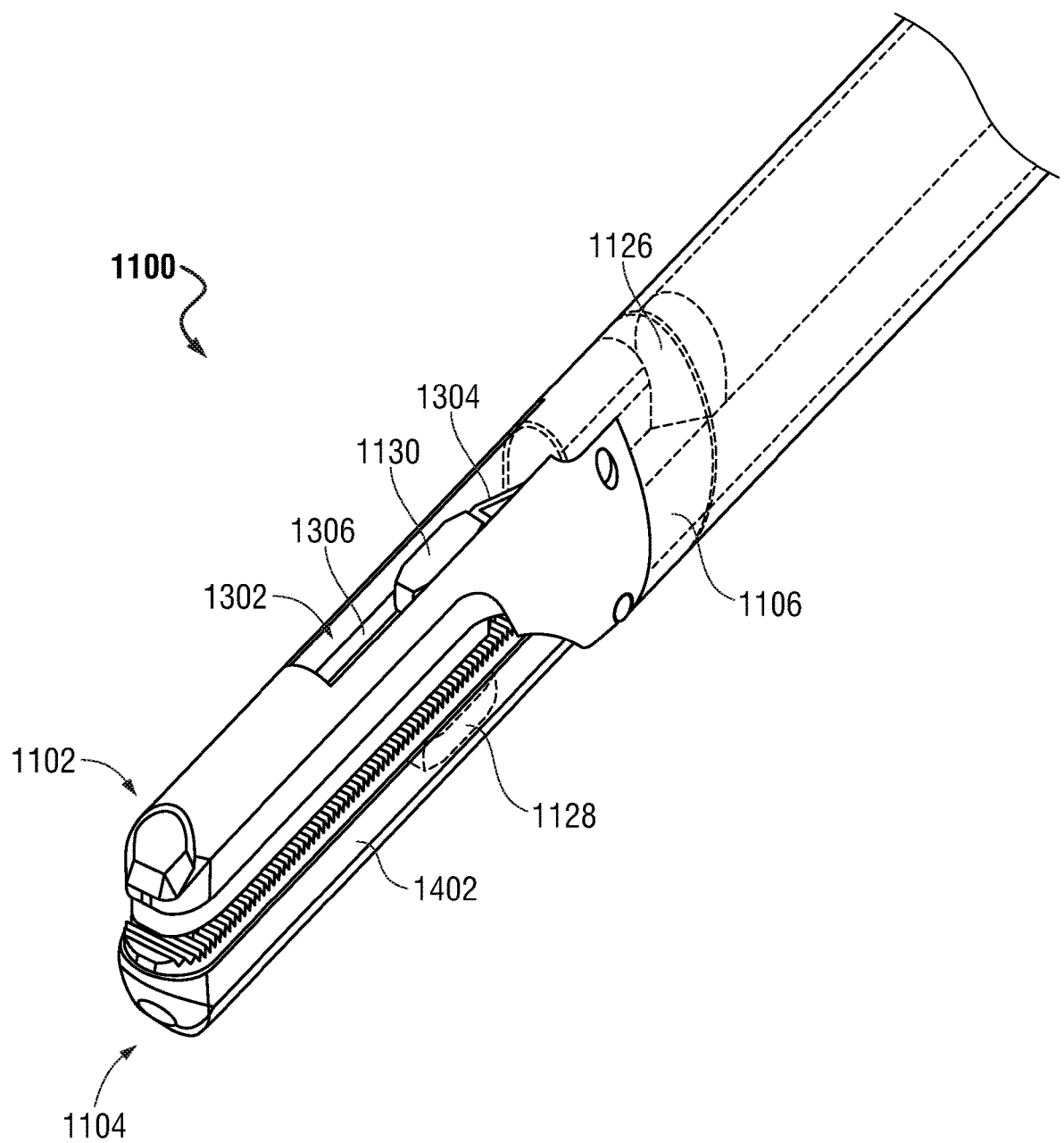
FIG. 14 is a partially transparent, perspective view of the ultrasonic cutting and cauterizing device of FIG. 13.

FIG. 14 shows a partially transparent view of the ultrasonic surgical device of FIGS. 11-13. The partially transparent view shows the lower recessed area 1402 where the lower protrusion 1128 travels when the waveguide 1126 is extended out of the shaft 1106.

Figure 15:
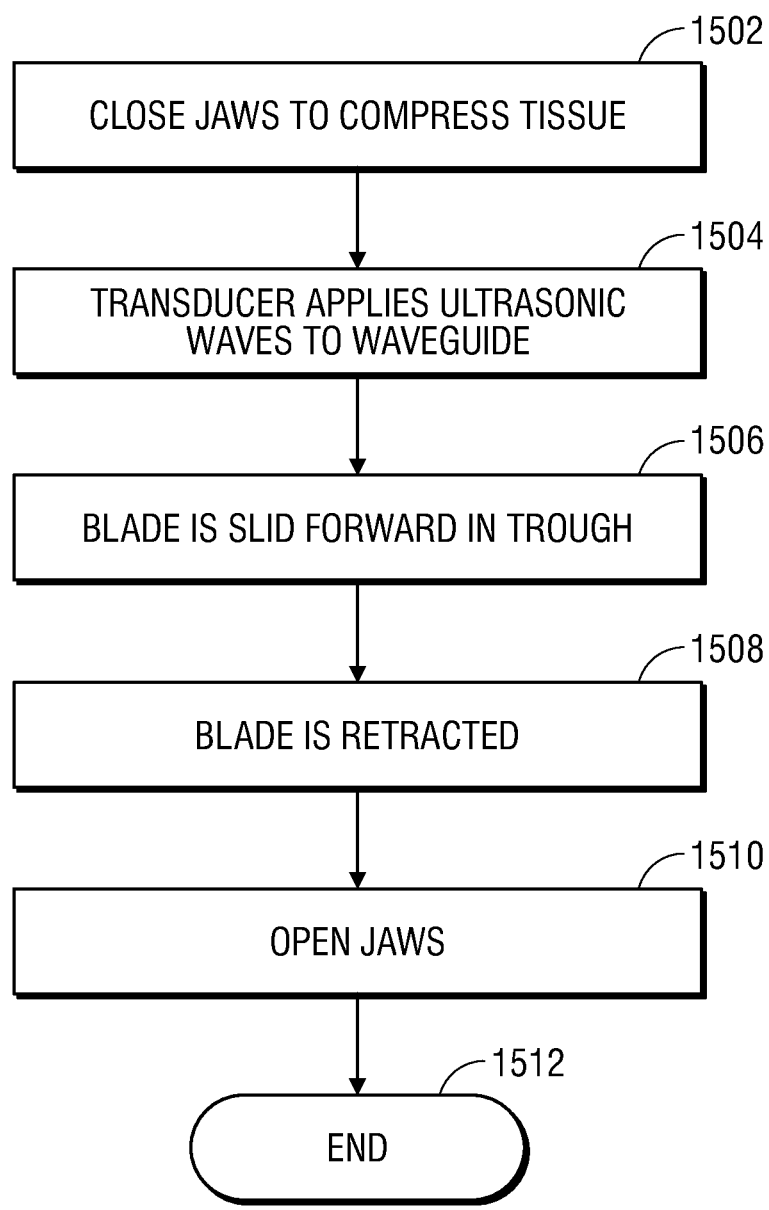
FIG. 15 is a process flow diagram of an exemplary process of operating an ultrasonic cutting and cauterizing device in accordance with an embodiment of the present invention.

FIG. 15 shows an exemplary process flow diagram of method of using an embodiment of the present invention. In a first step 1502, the operator closes the jaws 1102 and 1104 to compress tissue between them. Next, in step 1504, the ultrasonic transducer 702 applies an ultrasonic wave to the ultrasonic waveguide 500. In a following step, 1506, the blade portion 902, 904, 906 is slid within the trough 310 in a direction from the proximal end of the lower jaw to the distal end of the lower jaw to further compress and cut the already partially compressed tissue. Once step 1506 is complete, the blade, in step 1508, is retracted and, in step 1510, the jaws are opened and the tissue released. The process ends at step 1512.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the systems and methods. However, the systems and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems and methods as defined by the following claims.

What is claimed is:

1. A method of surgically treating tissue, comprising:
   compressing tissue between two opposing jaws disposed at a distal end of an ultrasonic instrument;
   applying a resonant ultrasonic wave to an ultrasonic waveguide of the ultrasonic instrument; and
   moving the ultrasonic waveguide longitudinally in a distal direction to advance the ultrasonic waveguide between at least a portion of the jaws to treat the tissue compressed between the jaws.

2. The method according to claim 1, wherein:
   the ultrasonic instrument comprises a shaft having an internal lumen that defines a longitudinal axis; and
   the ultrasonic waveguide is slidably disposed within the internal lumen of the shaft and is advanceable in the distal direction and retractable in a proximal direction along the longitudinal axis.

3. The method according to claim 2, wherein:
   the shaft has a proximal end; and
   the ultrasonic instrument further comprises a handle body at the proximal end of the shaft, the handle body comprising a movement mechanism configured to advance and retract the ultrasonic waveguide.

4. The method according to claim 3, wherein the two opposing jaws comprise:
   a first jaw fixed relative to the shaft; and
   a second jaw pivotally connected to the shaft and movable between open and closed positions with respect to the first jaw such that compressing the tissue between the two opposing jaws includes pivoting the second jaw towards the first jaw to move from the open position to the closed position.

5. The method according to claim 4, wherein the first jaw is one of fixedly connected to the shaft or integral with the shaft.

6. The method according to claim 4, wherein:
   the ultrasonic waveguide has a distal blade; and
   the first jaw has a distal end defining a trough,
   wherein advancing the ultrasonic waveguide between at least a portion of the two opposing jaws extends the distal blade into the trough.

7. The method according to claim 6, wherein:
   the distal blade has:
      proximal and distal ends;
      a sloped surface sloping upwardly from the distal end of the blade towards the proximal end of the blade and having an upper portion; and
      a substantially horizontal top surface at the upper portion, at least one of the sloped surface or the top surface forming a tissue-treating surface,
   wherein the distal blade further compresses and treats the tissue compressed between the jaws upon the advancing of the ultrasonic waveguide between at least the portion of the jaws and into the trough.

8. The method according to claim 4, wherein:
   the second jaw is connected to the shaft by at least one pivot; and
   the ultrasonic instrument further comprises a sheath surrounding the shaft and operatively connected to the at least one pivot, the sheath configured to move relative to the shaft in the distal direction to cause the second jaw to move about the pivot towards the first jaw towards the closed position.

9. The method according to claim 3, wherein the movement mechanism of the handle body comprises a trigger assembly operatively connected to the ultrasonic waveguide.

10. The method according to claim 3, wherein the handle body further comprises:
    an ultrasonic transducer operatively coupled to the ultrasonic waveguide to impart the resonant wave to the waveguide when activated; and
    a battery configured to activate the ultrasonic transducer.

11. A method of surgically treating tissue, comprising:
    applying a resonant ultrasonic wave to an ultrasonic waveguide of an ultrasonic instrument; and
    moving the ultrasonic waveguide in a distal direction:
       to move at least one jaw of two opposing jaws disposed at a distal end of the ultrasonic instrument from an open position to a closed position to compress tissue between the jaws; and
       to advance the ultrasonic waveguide between at least a portion of the closed jaws to treat the tissue compressed between the jaws.

12. The method according to claim 11, wherein:
    the ultrasonic instrument comprises a shaft having an internal lumen that defines a longitudinal axis; and
    the ultrasonic waveguide is slidably disposed within the internal lumen of the shaft and is advanceable in the distal direction and retractable in a proximal direction along the longitudinal axis.

13. The method according to claim 12, wherein:
    the shaft has a proximal end; and
    the ultrasonic instrument further comprises a handle body at the proximal end of the shaft, the handle body comprising a movement mechanism configured to advance and retract the ultrasonic waveguide.

14. The method according to claim 13, wherein the two opposing jaws comprise:
    a first jaw fixed relative to the shaft; and a second jaw pivotally connected to the shaft and movable with respect to the first jaw such that moving the at least one jaw from the open position to the closed position comprises pivoting the second jaw towards the first jaw.

15. The method according to claim 14, wherein:
the ultrasonic waveguide has a distal blade; and
the first jaw has a distal end defining a trough,
wherein advancing advancing the ultrasonic waveguide between at least a portion of the two opposing jaws extends the distal blade into the trough.

16. The method according to claim 15, wherein:
the distal blade has:
  proximal and distal ends;
  a sloped surface sloping upwardly from the distal end of the blade towards the proximal end of the blade and having an upper portion; and
  a substantially horizontal top surface at the upper portion, at least one of the sloped surface or the top surface forming a tissue-treating surface,
wherein the distal blade further compresses and treats the tissue compressed between the jaws upon the advancing of the ultrasonic waveguide between at least a portion of the jaws and into the trough.

17. The method according to claim 14, wherein:
the second jaw has a ramp therein; and
the ultrasonic waveguide has an upwardly-extending protrusion that is sized to engage with the ramp and place a closing force on the second jaw as the ultrasonic waveguide moves in the distal direction.

18. The method according to claim 17, wherein the protrusion has an I-beam shape.

19. The method according to claim 13, wherein the movement mechanism of the handle body comprises a trigger assembly operatively connected to the ultrasonic waveguide.

20. The method according to claim 13, wherein the handle body further comprises:
an ultrasonic transducer operatively coupled to the ultrasonic waveguide to impart the resonant wave to the waveguide when activated; and
a battery configured to activate the ultrasonic transducer.

* * * * *